(12) United States Patent
Falahee

(10) Patent No.: US 8,696,706 B2
(45) Date of Patent: Apr. 15, 2014

(54) PERCUTANEOUS LOCKING BONE FIXATION SYSTEM

(75) Inventor: Mark H. Falahee, Ann Arbor, MI (US)

(73) Assignee: Medical Designs, LLC, Ann Arbor, MI (US)

( * ) Notice: Subject to any disclaimer, the term of this patent is extended or adjusted under 35 U.S.C. 154(b) by 647 days.

(21) Appl. No.: 12/701,874

(22) Filed: Feb. 8, 2010

(65) Prior Publication Data

US 2010/0204700 A1 Aug. 12, 2010

Related U.S. Application Data

(60) Provisional application No. 61/150,339, filed on Feb. 6, 2009.

(51) Int. Cl.
*A61B 17/70* (2006.01)

(52) U.S. Cl.
USPC ............................................ 606/246; 411/29

(58) Field of Classification Search
USPC ................. 606/246–249, 279, 62–68; 411/29
See application file for complete search history.

(56) References Cited

U.S. PATENT DOCUMENTS

| | | | |
|---|---|---|---|
| 2,077,804 A | 4/1937 | Morrison | |
| 4,204,531 A * | 5/1980 | Aginsky | 606/63 |
| 4,736,560 A * | 4/1988 | Murphy | 52/410 |
| 4,760,843 A | 8/1988 | Fischer et al. | |
| 5,057,103 A * | 10/1991 | Davis | 606/63 |
| 5,098,433 A | 3/1992 | Freedland | |
| 5,458,599 A | 10/1995 | Adobbati | |
| 5,618,142 A * | 4/1997 | Sonden et al. | 411/29 |
| 6,506,051 B2 | 1/2003 | Levisman | |
| 6,648,890 B2 | 11/2003 | Culbert et al. | |
| 6,796,759 B2 * | 9/2004 | Aasgaard | 411/29 |
| 6,942,668 B2 | 9/2005 | Padget et al. | |
| 6,951,561 B2 | 10/2005 | Warren et al. | |
| 7,008,428 B2 | 3/2006 | Cachia et al. | |
| 7,608,094 B2 | 10/2009 | Falahee | |
| 7,645,279 B1 | 1/2010 | Haupt | |
| 2005/0240188 A1 | 10/2005 | Chow et al. | |
| 2006/0106393 A1 * | 5/2006 | Huebner et al. | 606/80 |
| 2006/0275097 A1 * | 12/2006 | Loi | 411/29 |
| 2009/0281580 A1 | 11/2009 | Emannuel | |

* cited by examiner

*Primary Examiner* — Matthew Lawson
*Assistant Examiner* — Si Ming Lee
(74) *Attorney, Agent, or Firm* — Gifford, Krass, Sprinkle, Anderson & Citkowski, P.C.

(57) ABSTRACT

A minimally invasive bone stabilization and locking system and method are applicable to joint fusion and fracture repair, including human facet joint stabilization. A bone-boring bit on an elongated shaft is used to drill a hole through the bone or joint such that the bit penetrates through the distal surface. An implant is provided having hollow body terminating in a spreadable distal end. The implant is placed over the elongated shaft and into the drilled hole such that the spreadable end protrudes through the distal surface. The elongated shaft is then pulled, such that the bit interacts with the distal end of the implant, thereby causing the spreadable end of the implant sleeve to spread so as to prevent backout of the implant body through the hole. A proximal cap may be tightened against the proximal surface, thereby fixing the bone or joint in compression.

4 Claims, 3 Drawing Sheets

PERCUTANEOUS LOCKING BONE FIXATION SYSTEM

REFERENCE TO RELATED APPLICATION

This application claims priority to U.S. Provisional Patent Application Ser. No. 61/150,339, filed Feb. 6, 2009, the entire content of which is incorporated herein by reference.

FIELD OF THE INVENTION

This invention relates generally to bone fixation and, in particular, to a minimally invasive bone stabilization and locking system that can be used for joint fusion and fracture repair.

BACKGROUND OF THE INVENTION

There are many instances wherein bones must be surgically fused as a result of trauma, degeneration, or other conditions. For example, for certain types of spinal stabilization, fusion of the facet joint may be indicated. One locking facet fixation system applicable to such procedures is described in U.S. Pat. No. 7,608,094. While quite effective, this system uses an "opposite side" approach with the necessary removal of at least a portion of the spinous process to achieve the appropriate trajectory for implant engagement and placement.

SUMMARY OF THE INVENTION

This invention resides in a minimally invasive bone stabilization and locking system and method applicable to joint fusion and fracture repair. The bone or joint may be a human facet joint.

In accordance with the invention, a method of fixing at least one bone or joint from a proximal surface to a distal surface, comprises the steps of providing a bone-boring bit on an elongated shaft and drilling a hole through the bone or joint such that the bit penetrates through the distal surface. An inventive implant is provided having hollow body terminating in a spreadable distal end. The implant is placed over the elongated shaft and into the drilled hole such that the spreadable end protrudes through the distal surface. The elongated shaft is then pulled, such that the bit interacts with the distal end of the implant, thereby causing the spreadable end of the implant sleeve to spread so as to prevent backout of the implant body through the hole.

The method may further include the steps of providing a proximal cap over the elongated shaft, and tightening the shaft against the proximal surface, thereby fixing the bone or joint in compression. The elongated shaft may include a threaded portion that extends out from the proximal surface, in which case the method includes providing and tightening a nut onto the threaded portion which bears against the proximal surface, thereby fixing the bone or joint in compression.

A system for fixing at least one bone or joint from a proximal surface to a distal surface comprises an implant having hollow body terminating in a spreadable distal end, and a bone-boring bit on an elongated shaft, the bit being shaped to interact with the spreadable distal end, such that when the shaft extends through the implant and the shaft is pulled in a proximal direction, the spreadable end of the implant sleeve spreads to prevent backout of the implant body. The system may further include a proximal cap coupled to the elongated shaft.

DETAILED DESCRIPTION OF THE INVENTION

This invention is directed to the minimally invasive delivery of a locking implant to fuse joints, repair fractures, and to perform other orthopaedic procedures. Thus, while the invention is described in terms of facet fixation, those of skill will appreciate that any bony fusion or fixation may be achieved with the same system and method. The preferred embodiments utilize a tube delivery system and, at least with respect to a set of facet joints at one level, a unilateral approach. In some cases the tube may, in fact, be optional. The overall goal is to achieve a small secure fixation or fusion, delivered under fluoroscopy through a small "stab wound," preferably with no bone removal required for placement.

Figure 1:
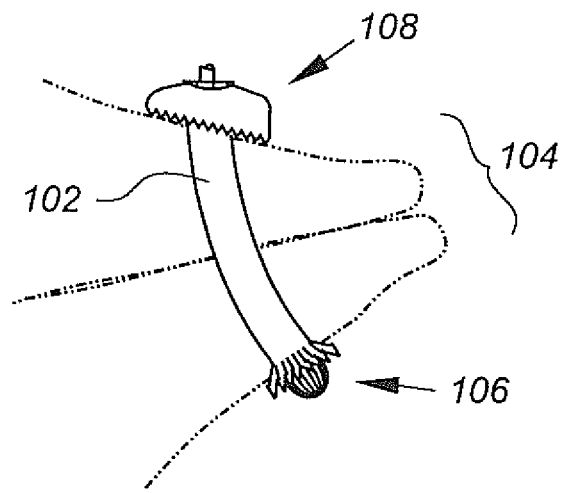
FIG. 1 is a drawing that illustrates an implant according to the invention.

FIG. 1 illustrates an implant according to the invention fusing a facet joint indicated with numerical reference 104. The implant broadly includes a hollow body portion 104 which may be curved, a distal spreading distal end 106, and a proximal cap 108 which may be angled or curved for improved conformity with bony surfaces. These components and preferred implantation methods will now be described in detail.

Figure 2:
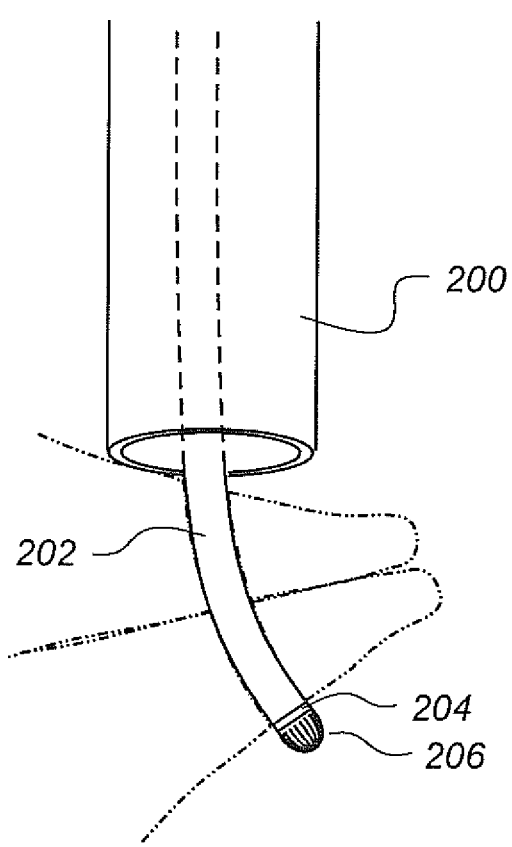
FIG. 2 is a drawing that begins a typical implantation procedure.
Figure 3:
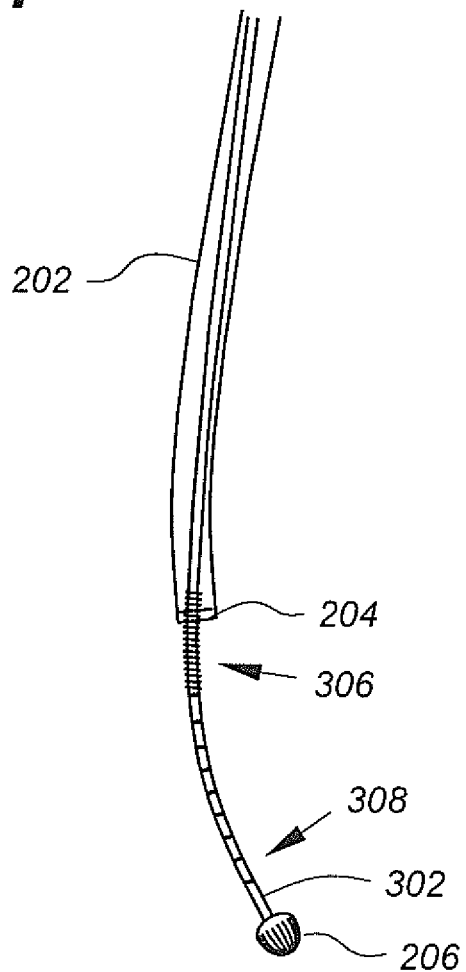
FIG. 3 shows a drill bit or burr on a flexible shaft, which may include a threaded portion and/or depth markings.

FIG. 2 begins a typical implantation procedure. An optional tube 200 is positioned with its distal end proximate a treatment site, and a drill sleeve 202 is brought in as shown. The sleeve and/or tube may be straight or curved, depending upon the procedure. The sleeve contains a cutting bit or burr 206, preferably having a rounded or "acorn" shape. Referring to FIG. 3, the bit is rotated with a flexible shaft 302, which may include a threaded portion 306 and/or depth markings 308 indicating the distance from base of the drill along the shaft in 1 and ½ cm increments, as one example. The threads may be limited to a given distance (i.e., 4 cm) from the drill tip, and the markings 308 may be present on the threads 306. The distal end of the sleeve may include a swivel washer 204 to reduce friction during rotational movement of the bit 206 through shaft 302. The base of drill burr engages with the drill sleeve washer tip which allows the sleeve to guide the burr in curvilinear fashion through the bone.

Figure 4:
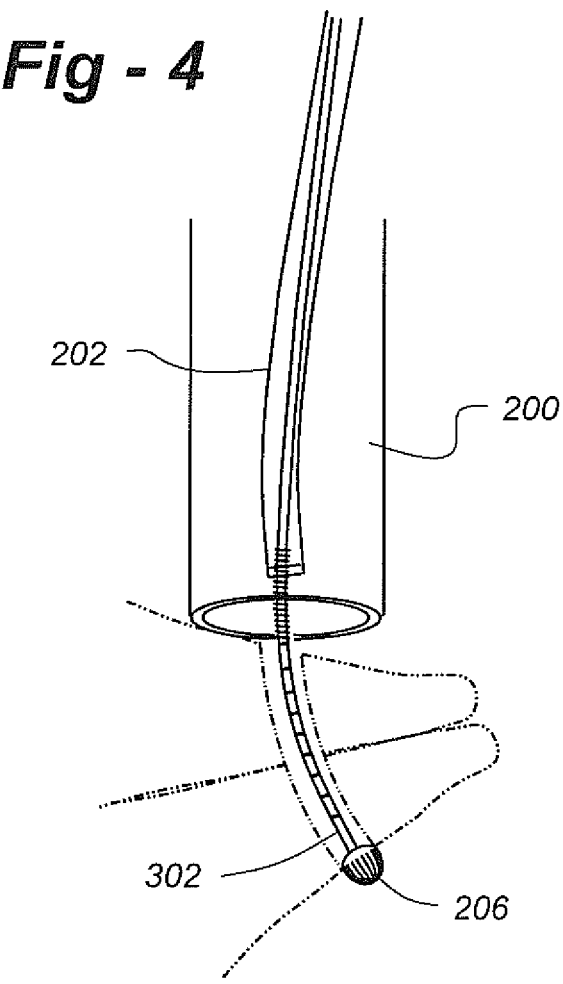
FIG. 4 illustrates a hole drilled through one or more bones and the drill sleeve being removed, leaving the drill burr attached to the elongated shaft.
Figure 5:
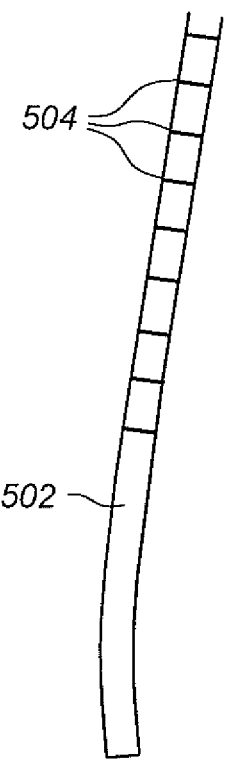
FIG. 5 depicts a flexible sleeve as an alternative to shaft markings.

As shown in FIG. 4, once a hole is drilled through one or more bones, the drill sleeve 202 is removed, leaving the drill burr 206 attached to the elongated shaft 302. The drill bit may be pulled back until it engages undersurface of facet (bone), with the depth of penetration being determined by reading the markings 308 on shaft 302. As an alternative to markings on shaft 302, a flexible sleeve 502 shown in FIG. 5, with markings 504 may be placed over the shaft 302 to determine depth. In some situations depth may be unimportant, in which case markings of any kind may be eliminated altogether.

Figure 6:
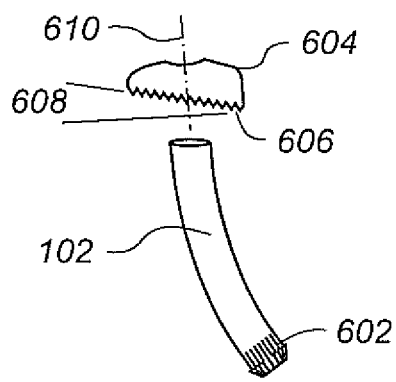
FIG. 6 is a more detailed drawing of the implant, which includes a hollow body portion, distal spreading tip, and cap.

FIG. 6 is a more detailed drawing of the implant, which includes a hollow body portion 102, distal spreading tip 602, and cap 604. The distal spreading tip of implant include fenestrated strips that may be tapered on the inside, with the wider opening toward the proximal end of the sleeve to accept the drill burr head. The outer tips of the fenestrated strips may be angled outward to catch against bone when locking compression is applied to shaft, as described in more detail below.

Figure 7:
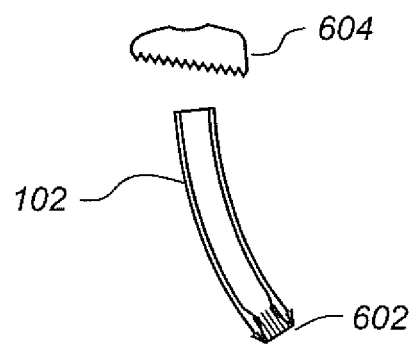
FIG. 7 is a cross section of an implant body.

The cap may include bone-engaging teeth 606, and may be angled as indicated at 608 relative to the axis 610 of the cap 604. FIG. 7 provides a cross section of the implant body 102. The implant may be made of any suitable material, including biocompatible metals and plastics, including organic polymer thermoplastics such as polyether ether ketone (PEEK). The delivery components disclosed herein may be made of any suitable sterilized metal or plastics.

Figure 8:
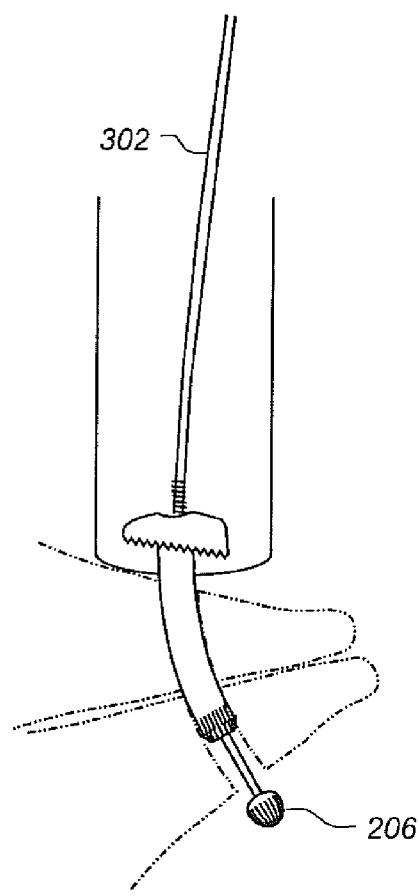
FIG. 8 illustrates an implant having the appropriate length body and adjustable proximal washer/cap being introduced into the hole drilled in the bone.

Referring now to FIG. 8, an implant having the appropriate length body and adjustable proximal washer/cap are introduced along the shaft 302 into the hole drilled in the bone. The body should fit securely along the shaft of the drill bit; that is, preferably with no 'play.' The proximal washer/cap may be rotated up to 360 degrees and angled in relation to the shaft to accommodate the varied surface of the proximal bone surface. Note that while the washer has various degrees of tilt and rotation in relation to the shaft, it is confined to the proximal aspect of the shaft, i.e., it cannot slide up and down shaft.

Figure 9:
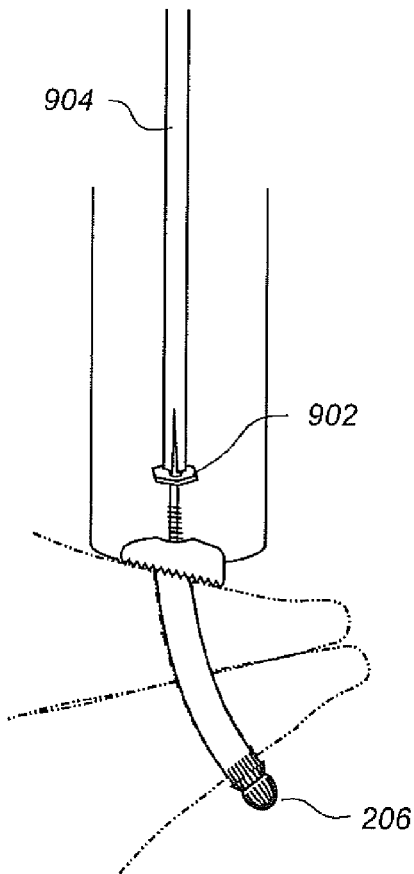
FIG. 9 depicts a locking nut being introduced with a wrench or holder 904, and the implant being secured to bone.
Figure 10:
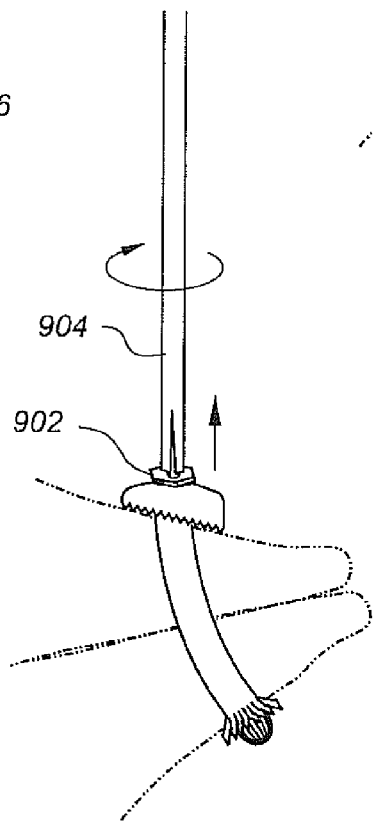
FIG. 10 shows how final tightening of the locking nut draws the drill burr base into the fenestrated end of the implant body.
Figure 11:
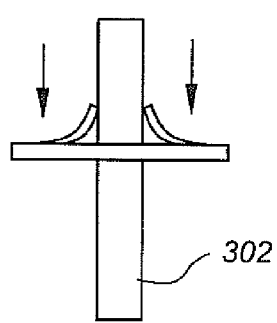
FIG. 11 is a drawing that shows a push-on crimping fastener used in lieu of a threaded connection.

In FIG. 9, a locking nut 902 is introduced with wrench or holder 904, and the implant is secured to bone. In particular, after the implant body has been introduced and the washer seated loosely against bone surface, the locking nut is placed over the elongated shaft and rotated into a secure position. Final tightening of the locking nut draws the drill burr base into the fenestrated component of the sleeve, as shown in FIG. 10. This causes the fenestrated strips to splay outward and capture against the undersurface of the bone. At the same time, the downward turning of the nut compresses the proximal washer onto the upper facet bone surface. Once the nut is secure, excess elongated shaft is cut flush to top of nut surface, and instruments may be removed. As an alternative to a threads 306 and nut 902, a push-on crimping fastener of the type shown in FIG. 11 may be used.

The invention claimed is:

1. A system for fixing at least one bone or joint from a proximal surface to a distal surface, comprising:
   a hollow implant body having a proximal end and a distal end terminating in a shaped spreadable end;
   a bone-boring bit on an elongated rotatable shaft, the bit having a distal surface with a burr or cutting edges and a proximal surface conforming to the shape of the spreadable end, such that when the bit extends through the implant body and past the distal end and the shaft is pulled in a proximal direction, the interaction of the proximal surface of the bit and the shaped, spreadable end of the implant body spreads the spreadable end to prevent backout of the implant body; and
   a proximal cap secured to the proximal end of the implant body thereby applying compression across the proximal and distal surfaces of the bone or joint.

2. The system of claim 1, wherein the proximal cap includes an angled or curved surface configured for conformity with the proximal surface of the bone or joint.

3. The system of claim 1, wherein the proximal cap includes bone-engaging teeth.

4. The system of claim 1, further including a push-on crimping fastener to apply compression to the proximal cap.

* * * * *